(12) United States Patent
Kamiyama et al.

(10) Patent No.: US 7,214,820 B2
(45) Date of Patent: May 8, 2007

(54) PROCESS FOR PRODUCING OPTICALLY ACTIVE FLURBIPROFEN

(75) Inventors: Shunji Kamiyama, Kobe (JP); Kazuto Yoshida, Ibo-gun (JP); Yasuo Chikusa, Himeji (JP); Jun Matsumoto, Kakogawa (JP); Keisuke Matsuyama, Kobe (JP)

(73) Assignee: Nagase & Co., Ltd., Osaka-shi (JP)

( * ) Notice: Subject to any disclaimer, the term of this patent is extended or adjusted under 35 U.S.C. 154(b) by 55 days.

(21) Appl. No.: 10/543,186

(22) PCT Filed: Jan. 20, 2004

(86) PCT No.: PCT/JP2004/000442

§ 371 (c)(1),
(2), (4) Date: Jul. 22, 2005

(87) PCT Pub. No.: WO2004/065344

PCT Pub. Date: Aug. 5, 2004

(65) Prior Publication Data

US 2006/0135617 A1 Jun. 22, 2006

(30) Foreign Application Priority Data

Jan. 23, 2003 (JP) ............................. 2003-014520

(51) Int. Cl.
*C07B 57/00* (2006.01)
(52) U.S. Cl. .................................... 562/402
(58) Field of Classification Search ..................... None
See application file for complete search history.

(56) References Cited

U.S. PATENT DOCUMENTS

| 3,755,427 A | 8/1973 | Adams et al. |
| 3,959,364 A | 5/1976 | Armitage et al. |
| 4,209,638 A | 6/1980 | Nicholson et al. |
| 5,190,981 A | 3/1993 | Wechter |
| 5,599,969 A * | 2/1997 | Hardy et al. ................. 562/401 |

FOREIGN PATENT DOCUMENTS

| EP | 0 703 212 | 3/1996 |
| GB | 1 596 032 | 8/1981 |
| JP | 54-154724 | 12/1979 |
| JP | 8-319252 | 12/1996 |
| WO | 94/12460 | 6/1994 |
| WO | 96/23759 | 8/1996 |

* cited by examiner

*Primary Examiner*—Thurman K. Page
*Assistant Examiner*—Yevgeny Valenrod
(74) *Attorney, Agent, or Firm*—Oblon, Spivak, McClelland, Maier & Neustadt, P.C.

(57) ABSTRACT

The present invention provides a method for producing optically active flurbiprofen. The method of the present invention includes mixing racemic flurbiprofen and (S)- or (R)-3-methyl-2-phenylbutylamine in an organic solvent to produce a diastereomeric salt; and treating the diastereomeric salt with an acid in a second solvent. In the method of the present invention, flurbiprofen having a desired absolute configuration can be obtained very efficiently without repeating the procedure for optical resolution a plurality of times.

10 Claims, No Drawings

PROCESS FOR PRODUCING OPTICALLY ACTIVE FLURBIPROFEN

TECHNICAL FIELD

The present invention relates to a method for producing optically active flurbiprofen. More specifically, the present invention relates to a method for efficiently producing flurbiprofen having an excellent optical purity from racemic flurbiprofen.

BACKGROUND ART

Flurbiprofen is a substance used as an antiphlogistic analgetica in the field of medicament, and especially it is known that (S)-flurbiprofen has an excellent efficacy (e.g., U.S. Pat. No. 5,190,981).

The flurbiprofen is generally produced in the form of a racemic compound. It is known that from the racemic compound, flurbiprofen having a high optical purity can be produced by an optical resolution method using, for example, an optically active amine compound (more specific example is α-phenylethylamine) as an optical resolution agent (e.g., Japanese Laid-Open Patent Publication No. 54-154724 and U.S. Pat. No. 4,209,638).

The above-described method using an optical resolution agent utilizes a difference in the physical properties between diastereomers, which are produced from a pair of enantiomer of a racemic flurbiprofen and another optically active substance.

However, with these methods, frequent resolution operations are necessary in order to improve the optical purity of flurbiprofen. For this reason, it was difficult to produce flurbiprofen having a desired optical purity efficiently.

When a racemic substance is subjected to optical resolution, a general rule is not known as to which antipode should be used as an optical resolution agent in order to selectively obtain a salt formed by the resolution agent and a desired enantiomer to provide a slightly soluble crystal. For this reason, in general, it is inevitable to repeat preliminary experiments many times in which various optical resolution agents are combined with various solvents with respect to a substance to be subjected to optical resolution. Therefore, it is very difficult to select a preferable optical resolution agent. Moreover, even if a relatively preferable optical resolution agent is specified in the above-described manner, it is necessary to perform resolution operations frequently. Therefore, there is a demand for development of a more efficient optical resolution method to increase the industrial productivity.

DISCLOSURE OF INVENTION

It is an objective of the present invention to provide a method for producing flurbiprofen having a desired absolute configuration from racemic flurbiprofen efficiently and with an excellent optical purity.

The present invention provides a method for producing optically active flurbiprofen, and the method includes mixing racemic flurbiprofen and (S) or (R)-3-methyl-2-phenylbutylamine in an organic solvent to produce a diastereomeric salt; and treating the diastersomeric salt with an acid in a second solvent.

In a preferable embodiment, in the step of producing a diastereomeric salt, (S)-3-methyl-2-phenylbutylamine is used.

In a preferable embodiment, the organic solvent is at least one solvent selected from the group consisting of $C_1$ to $C_3$ alcohol, toluene, and xylene.

In a preferable embodiment, the organic solvent is a water-containing solvent.

In a more preferable embodiment, the water-containing solvent is an organic solvent that contains water at a ratio of 20 v/v % or less.

In a preferable embodiment, the second solvent is a hydrophobic solvent or water.

The present invention also provides a diastereomeric salt obtained by mixing (S)- or (R)-3-methyl-2-phenylbutylamine and racemic flurbiprofen in an organic solvent.

In a preferable embodiment, the 3-methyl-2-phenylbutylamine has an S-configuration.

The present invention also provides a diastereomeric salt represented by the following formula (I):

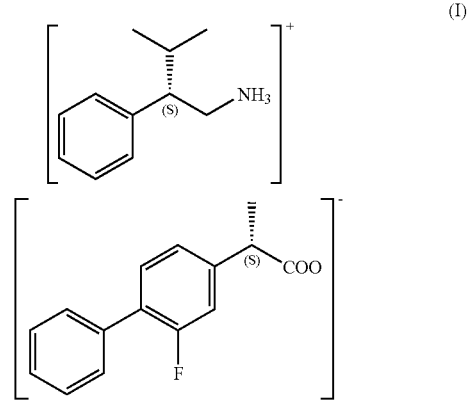

The present invention also provides a diastereomeric salt represented by the following formula (II):

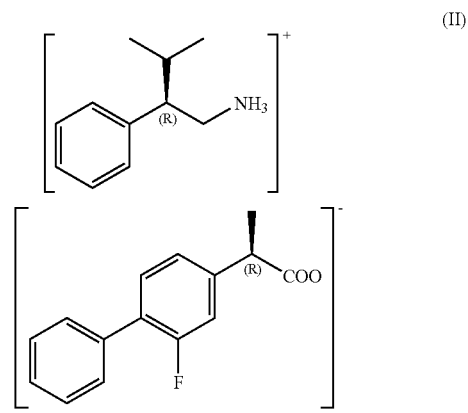

BEST MODE FOR CARRYING OUT THE INVENTION

In the method for producing optically active flurbiprofen of the present invention, first, racemic flurbiprofen and (S)- or (R)-3-methyl-2-phenylbutylamine are mixed in an organic solvent to form a diastereomeric salt.

The racemic flurbiprofen used in the present invention can be produced by a method that is known to those skilled in the art, and can be produced by, for example, a method described in U.S. Pat. No. 3,755,427 or 3,959,364. The term "racemic flurbiprofen" used in this specification refers to a mixture of (S)-flurbiprofen and (R)-flurbiprofen, and includes not only a mixture of (S)-flurbiprofen and (R)-flurbiprofen at a molar ratio of 50:50, but also a mixture of (S)-flurbiprofen and (R)-flurbiprofen at a molar ratio from 20:80 to 80:20, preferably from 30:70 to 70:30.

The 3-methyl-2-phenylbutylamine used in the present invention serves as an optical resolution agent, and is either (S)-3-methyl-2-phenylbutylamine or (R)-3-methyl-2-phenylbutylamine. In the present invention, (S)-3-methyl-2-phenylbutylamine or (R)-3-methyl-2-phenylbutylamine is selected, depending on the absolute configuration of an optically active flurbiprofen that is desired to be produced. That is to say, when (S)-flurbiprofen is to be produced from racemic flurbiprofen, (S)-3-methyl-2-phenylbutylamine is used, and when (R)-flurbiprofen is to be produced, (R)-3-methyl-2-phenylbutylamine is used.

In the present invention, in order to increase the optical purity of (S)- or (R)-flurbiprofen, it is preferable to use (S)- or (R)-3-methyl-2-phenylbutylamine having a high optical purity. In either (S)-3-methyl-2-phenylbutylamine or (R)-3-methyl-2-phenylbutylamine, the optical purity is preferably 70% ee or more, more preferably 80% ee or more, and even more preferably 90% ee or more.

There is no particular limitation regarding the amount of (S)- or (R)-3-methyl-2-phenylbutylamine used. The amount is preferably 0.6 moles or more, more preferably 0.6 moles to 2 moles, with respect to 1 mole of a desired enantiomer (that is, (S)- or (R)-flurbiprofen) contained in the racemic flurbiprofen used. It is more preferable to set the amount in the range from 0.8 moles to 1.2 moles in order to reduce the amount of the optical resolution agent used.

In the present invention, formation of a diastereomeric salt from racemic flurbiprofen and (S)- or (R)-3-methyl-2-phenylbutylamine in the above-described manner is performed in an organic solvent. Specific examples of the organic solvent used herein include aromatic solvents such as benzene, toluene, and xylene; lower alcohols such as methyl alcohol, ethyl alcohol, propyl alcohol, butyl alcohol, isopropyl alcohol, and isobutyl alcohol, esters such as ethyl acetate; and ethers such as isopropyl ether and methyl-tert-butyl ether; and combinations thereof. In particular, it is preferable to use $C_1$ to $C_8$ alcohols and/or solvents of aromatic hydrocarbon such as toluene or xylene. The organic solvent used in the present invention may be a water-containing solvent that contains water in view of production of flurbiprofen having a high optical purity. When a water-containing solvent is used, the ratio of water (water content) with respect to the entire solvent is 20 v/v % or less, preferably 0.01 v/v % to 20 v/v %, more preferably 10 v/v % to 20 v/v %. By using such a water-containing solvent, the optical purity of the flurbiprofen after optical resolution can be improved further. In the present invention, it is more preferable to use as the organic solvent $C_1$ to $C_8$ alcohols having a water content of 10 v/v % to 20 v/v %.

The amount of an organic solvent used in the present invention can be selected as appropriate by those skilled in the art, and there is no particular limitation.

More specifically, the diastereomeric salt can be formed by either one of the following procedures: The racemic flurbiprofen is dissolved, for example, in an organic solvent as described above with warming, and then a predetermined amount of (S)- or (R)-3-methyl-2-phenylbutylamine is added to this solution with stirring; (S)- or (R)-3-methyl-2-phenylbutylamine is dissolved, for example with warming, in an organic solvent, and then a predetermined amount of the racemic flurbiprofen is added to this solution with stirring; alternatively, a solution in which the racemic flurbiprofen is dissolved, for example with warming, in an organic solvent, and a solution in which (S)- or (R)-3-methyl-2-phenylbutylamine is dissolved, for example with warming, in another organic solvent are prepared separately, and thereafter these solutions are mixed with stirring. A specific temperature for warming depends on the kind of the organic solvent used, so that there is no particular limitation.

Thereafter, by cooling this solution slowly, a diastereomeric salt is formed from the (S)- or (R)-3-methyl-2-phenylbutylamine in the solution and flurbiprofen having the same absolute configuration as (S)- or (R)-3-methyl-2phenylbutylamine, and is precipitated preferentially.

For example, when (S)-3-methyl-2-phenylbutylamine is used, the diastereomeric salt that is precipitated in the present invention is a salt of (S)-3-methyl-2-phenylbutylamine and (S)-flurbiprofen in the racemic compound, for example, represented by formula (I) below.

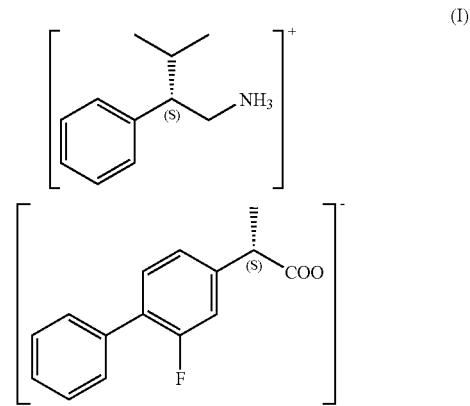

On the other hand, when (R)-3-methyl-2-phenylbutylamine is used, the diastereomeric salt precipitated in the present invention is a salt of (R)-3-methyl-2-phenylbutylamine and (R)-flurbiprofen in the racemic compound, for example, represented by formula (II) below.

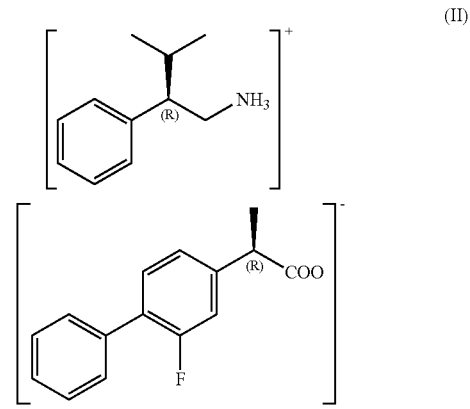

The two diastereomeric salts are both insoluble in the organic solvents used, and as a result, are precipitated in the organic solvents.

After the diastereomeric salt is precipitated, this salt can be removed easily, for example, by filtration. The diastereomeric salt collected by filtration may be recrystallized, if necessary.

In the method for producing optically active flurbiprofen of the present invention, then, the obtained diastereomeric salt is treated with an acid in a second solvent.

The second solvent used in the present invention is a hydrophobic solvent or water. Examples of hydrophobic solvents include benzene, toluene, xylene, ethyl acetate, ethyl ether, isopropyl ether, dichloroethane, trichloroethane, hexane, heptane, and octane. When a hydrophobic solvent is used, there is no particular limitation on the kind, as long as it can dissolve flurbiprofen to be obtained.

In the present invention, the diastereomeric salt is added and dispersed in the second solvent, and then an acid is added thereto. Alternatively, a dispersion of the diastereomeric salt in the second solvent may be added to an acid.

Examples of the acid used in the present invention include (diluted) hydrochloric acid, (diluted) sulfuric acid, and (diluted) nitric acid. There is no particular limitation on the amount of the acid used, and an appropriate amount can be selected by those skilled in the art.

The diastereomeric salt is subjected to metathesis by adding the acid, so that an optically active flurbiprofen having a desired absolute configuration can be obtained.

Thereafter, another treatment for recovering the optically active flurbiprofen is performed.

First, a recovery treatment will be described when a hydrophobic solvent is used as the second solvent.

After the metathesis by the addition of the acid, an appropriate amount of a hydrophobic solvent as described above is further added to the reaction mixture, and then the reaction mixture is subjected to extraction. Then, the oil layer is collected, and if necessary, washed with water and dried by a method used by those skilled in the art. Thereafter, under a reduced pressure, the solvent is removed and the resultant product may be recrystallized, for example, using a solvent made of petroleum hydrocarbon such as hexane, heptane, and octane. In this manner, a desired optically active flurbiprofen having an improved optical purity can be obtained.

Next, a recovery treatment will be described when water is used as the second solvent.

In this case, after the metathesis by the addition of the acid, the product precipitated from the reaction mixture is filtrated, so that a desired optically active flurbiprofen having an improved optical purity can be obtained.

The optically active flurbiprofen obtained by the present invention has an optical purity of preferably 80% ee or more, more preferably 90% as or more by being subjected to this series of processes. Thus, an optically active flurbiprofen in question can be produced very efficiently without repeating series of processes.

It should be noted that after the metathesis by the addition of the acid, flurbiprofen having the other absolute configuration that remains in the reaction mixture (e.g., (R)-flurbiprofen that remains in the reaction mixture when (S)-flurbiprofen is produced from a racemic flurbiprofen) can be easily regenerated into racemic flurbiprofen, for example, by using a method disclosed in WO96/23759. Therefore, by performing the method of the present invention again, using the racemic flurbiprofen obtained by regeneration, flurbiprofen (e.g., (S)-flurbiprofen) having a desired optical activity can be obtained. As a result, the total yield of the optically active flurbiprofen can be increased further.

Hereinafter, the present invention will be described by way of examples, but is not limited to the examples.

EXAMPLE 1

First, 2 g (8.2 mmol) of racomic flurbiprofen and 0.67 g (4.1 mmol) of (S)-3-methyl-2-phenylbutylamine were added to 6 mL of toluene (first solvent) and dissolved therein by heating while stirring. After a homogeneous solution was obtained, it was cooled with stirring.

After cooling, crystals were precipitated in the solution. The solution containing the precipitated crystals was stirred at room temperature for 30 minutes, and then the crystals were filtrated. The obtained crystals were washed with toluene (1 mL×3) and dried to give white crystals (diastereomeric salt). The amount of the diastereomeric salt produced was 1.07 g (yield: 32.1%, which was based on the racemic flurbiprofen used), and the melting point was 178.6° C. to 180.0° C.

Then, a part of thus-obtained diastersomeric salt was dispersed in toluene and diluted hydrochloric acid was added thereto. Thereafter, the reaction product was extracted with toluene, and washed with water and dried, and then the toluene was removed by distillation under a reduced pressure. Then, the residue was crystallized in hexane to give white crystals. By analyzing optical rotation of the obtained crystals, the crystals were confirmed to be (S)-flurbiprofen. The optical purity of the obtained (S)-flurbiprofen was 96.9% ee.

The optical purity was measured by high performance liquid chromatography under the following conditions: CHIRALCEL OJ-R (manufactured by DAICEL CHEMICAL INDUSTRIES, LTD.) was used; 0.2 M $H_3PO_4 \cdot KH_2PO_4$ buffer (pH 2)/acetonitrile=65/35 (v/v) was used as the mobile phase; and the flow rate was 0.5 mL/min. The detection wavelength was UV 254 nm, and the measurement was performed at room temperature.

EXAMPLES 2 TO 10

(S)-Flurbiprofen was obtained in a similar manner to that described in Example 1, except that the toluene used as the first solvent in Example 1 was replaced by first solvents shown in Table 1. The first solvent used in each example, the yield of the obtained diastereomeric salt and the optical purity of the obtained (S)-flurbiprofen are shown in Table 1.

TABLE 1

|  | First solvent | Yield of diastereomeric salt *[1] (%) | Optical purity of (S)-flurbiprofen (% ee) |
| --- | --- | --- | --- |
| Example 2 | Methanol | 25.8 | 97.1 |
| Example 3 | Ethanol | 37.7 | 96.9 |
| Example 4 | Isopropanol | 44.9 | 58.5 |
| Example 5 | Ethyl acetate | 40.7 | 75.3 |
| Example 6 | Water-containing methanol (volume ratio of methanol and water = 9:1) | 29.1 | 98.5 |
| Example 7 | Water-containing ethanol (volume ratio of ethanol and water = 9:1) | 33.6 | 98.4 |
| Example 8 | Isopropyl ether | 47.5 | 53.5 |
| Example 9 | Methyl t-butyl ether | 48.8 | 55.8 |
| Example 10 | o-Xylene | 29.7 | 96.2 |

*[1] Yield is based on the racemic flurbiprofen used.

As shown in Table 1, all of the diastereomeric salts obtained in Examples 2 to 10 can be obtained at a high yield (theoretical maximum value is 50%) as in Example 1, and it shows that the (S)-3-methyl-2-phenylbutylamine forms a salt efficiently with (S)-flurbiprofen in the racemic compound. Furthermore, the optical purity of the (S)-flurbiprofen obtained in Examples 2 to 10 was all high, and the optical activity was increased by performing only once of processes. In particular, in the system employing methanol (Example 2), ethanol (Example 3) and solvents containing these solvents and water (Examples 6 and 7), and in the system employing an aromatic hydrocarbon solvent such as toluene (Example 1) and xylene (Example 10), (S)-flurbiprofen with particularly high optical purity could be produced which can satisfy the use of the (S)-flurbiprofen as pharmaceuticals.

EXAMPLE 11

First, 150 g (614 mmol) of racemic flurbiprofen and 50 g (307 mmol) of (S)-3-methyl-2-phenylbutylamine were added to 300 mL of 90% (v/v) isopropyl alcohol aqueous solution and dissolved therein by heating with stirring. Thereafter, this solution was cooled to room temperature with stirring.

After cooling, crystals were precipitated in the solution. The solution containing the precipitated crystals was further stirred at room temperature for 30 minutes, and then the crystals were filtrated. The obtained crystals were washed with 90% (v/v) isopropanol aqueous solution (30 mL×3) and dried to give white crystals (diastereomeric salt). The amount of the diastereomeric salt produced was 95.4 g (yield: 38.1%, which was based on the racemic flurbiprofen used).

Then, a part of the obtained diastereomeric salt was subjected to metathesis and crystallization in the same manner as in Example 1 to give crystals of (S)-flurbiprofen. The optical purity of the obtained (S)-flurbiprofen was 94.7% ee.

The optical purity of this (S)-flurbiprofen was confirmed and then, again, 80 g of white crystals of the obtained diastereomeric salt was added to 300 mL of 90% (v/v) isopropyl alcohol aqueous solution and dissolved therein by heating, and then cooled to room temperature with stirring for recrystallization. After the solution containing the precipitated crystals was stirred for 30 minutes, the crystals were filtrated. The obtained crystals were washed with 90% (v/v) isopropanol aqueous solution (30 mL×8) and dried to give white crystals (purified diastereomeric salt). The amount of the purified diastereomeric salt produced was 75.2 g (yield: 94%, which was based on the diastereomeric salt that had been subjected to recrystallization).

Then, a part of the purified diastereomeric salt was subjected to metathesis and crystallization in the same manner as in Example 1 to give crystals of (S)-flurbiprofen. The optical purity of the obtained (S)-flurbiprofen was more than 99.5% ee.

INDUSTRIAL APPLICABILITY

According to the present invention, flurbiprofen having a high optical purity can be produced from racemic flurbiprofen in a reduced number of processes. In the method of the present invention, there is no need of repeating the procedure for optical resolution a plurality of times, and flurbiprofen having a desired absolute configuration can be obtained very efficiently.

The invention claimed is:

1. A method for producing optically active flurbiprofen which comprises:
    mixing racemic flurbiprofen and (S)- or (R)-3-methyl-2-phenylbutylamine in an organic solvent to produce a diastereomeric salt; and
    treating the diastereomeric salt with an acid in a second solvent.

2. The method according to claim 1, wherein in the step of producing a diastereomeric salt, (S)-3-methyl-2-phenylbutylamine is used.

3. The method according to claim 1, wherein the organic solvent is at least one solvent selected from the group consisting of $C_1$ to $C_3$ alcohol, toluene, and xylene.

4. The method according to claim 1, wherein the organic solvent is a water-containing solvent.

5. The method according to claim 4, wherein the water-containing solvent is an organic solvent that contains water at a ratio of 20 v/v % or less.

6. The method according to claim 1, wherein the second solvent is a hydrophobic solvent or water.

7. A diastereomeric salt obtained by mixing (S)- or (R)-3-methyl-2-phenylbutylamine and racemic flurbiprofen in an organic solvent.

8. The diastereomeric salt according to claim 7, wherein the 3-methyl-2-phenylbutylamine has an S-configuration.

9. A diastereomeric salt represented by the following formula (I):

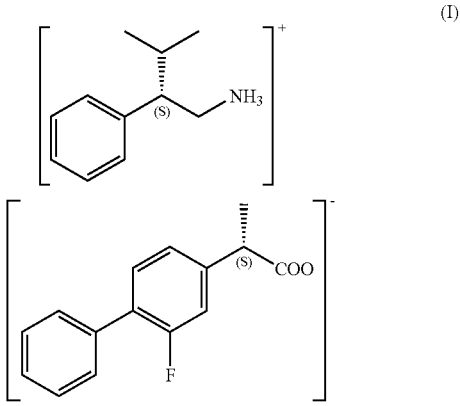

10. A diastereomeric salt represented by the following formula (II):

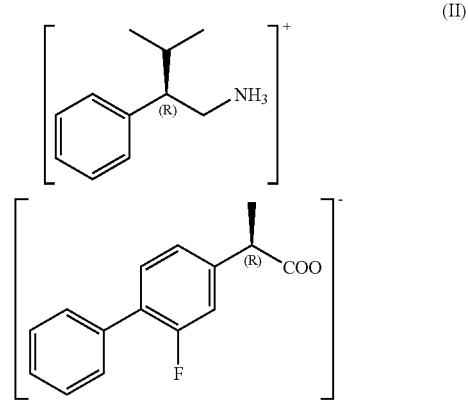

* * * * *